United States Patent [19]

Halasz et al.

[11] 4,021,486
[45] May 3, 1977

[54] HYDROXYALKYL-AMINO NITRODIPHENYLAMINE COMPOUNDS USEFUL AS HAIR DYES

[75] Inventors: Alexander Halasz, Norwalk; David Cohen, Stamford, both of Conn.

[73] Assignee: Clairol Incorporated, New York, N.Y.

[22] Filed: Jan. 14, 1975

[21] Appl. No.: 540,780

Related U.S. Application Data

[62] Division of Ser. No. 318,293, Dec. 26, 1972, Pat. No. 3,950,127.

[52] U.S. Cl. .................................. 260/573; 8/10; 8/10.1; 8/10.2; 260/471 A; 260/558 P; 260/571; 260/574; 260/576; 260/578; 424/47
[51] Int. Cl.$^2$ .................. C07C 91/40; A61K 7/13
[58] Field of Search ............. 260/571, 573; 8/10.1, 8/10.2, 11

[56] References Cited

UNITED STATES PATENTS

| | | | |
|---|---|---|---|
| 2,013,182 | 9/1935 | Laska et al. | 260/571 X |
| 2,069,039 | 1/1937 | Laska et al. | 260/571 X |
| 2,202,902 | 6/1940 | Ellis et al. | 260/573 X |
| 3,168,442 | 2/1965 | Brunner et al. | 260/573 X |
| 3,274,249 | 9/1966 | Brunner et al. | 260/573 X |

OTHER PUBLICATIONS

Bach, et al., Index Chemicus, vol. 27, 86981 (1967).
Abramovitch, et al., Index Chemicus, vol. 28, 92631 (1968).

*Primary Examiner*—Daniel E. Wyman
*Assistant Examiner*—John J. Doll
*Attorney, Agent, or Firm*—Irving Holtzman; George A. Mentis; David J. Mugford

[57] ABSTRACT

Compounds useful as hair dyes of the formula:

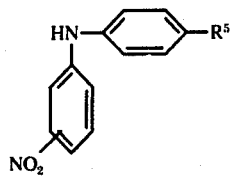

in which $R^5$ is OH, -NH(lower hydroxyalkyl), -N(lower hydroxyalkyl)$_2$ or -O lower alkyl.

5 Claims, No Drawings

HYDROXYALKYL-AMINO NITRODIPHENYLAMINE COMPOUNDS USEFUL AS HAIR DYES

This is a division of application Ser. No. 318,293 filed Dec. 26, 1972, now U.S. Pat. No. 3,950,127.

This invention relates to certain hair dye compositions and to methods for dyeing hair using these compositions. More particularly, it concerns hair dye compositions and hair dyeing methods which are useful in dyeing human hair and especially living human hair on the head. This invention also relates to certain novel compounds which are useful as hair dyes.

In preparing hair dye compositions for human hair of the direct-dyeing type, it is frequently necessary to blend dyes having a yellow to orange or red shade with other colors to obtain a desired natural looking shade. It has been common practice in this art to use certain nitro-p-phenylenediamines for this purpose since they are readily soluble or dispersible in water and diffuse easily into the hair. Typical of these compounds are 2-nitro-p-phenylenediamine, N'-methyl-2-nitro-p-phenylenediamine, N'-(β-hydroxyethyl)-2-nitro-p-phenylenediamine. These dyes, however, leave much to be desired with respect to their fastness to shampooing. Although these compounds have enough affinity to permanent waved hair and give good dyeing, initially their wash fastness is very poor even on one shampooing.

Other yellow to orange or red dyes are also known in the prior art which are of the azo and anthraquinone dye classes. These, however, have too low a dispersibility in water or affinity for hair to be useful. This is thought to be due to the large molecular size of these dyes which prevents them from readily diffusing into hair.

It has now been found that a certain class of nitrodiphenylamine dyes, defined more particularly below, provide a class of yellow to orange and red dyes which have the advantage that they have good affinity for damaged hair, especially permanent waved hair, and yet have greater shampoo fastness than the prior art nitrophenylenediamine dyes used in this art for this purpose.

It is, accordingly, an object of the present invention to provide hair dye compositions containing as a dye component certain nitrodiphenylamines defined more particularly below.

It is also an object of this invention to provide a method for dyeing hair, and particularly living human hair on the head using the aforesaid hair dye compositions.

It is still a further object of this invention to provide certain novel compounds which are useful as hair dyes and particularly as direct-dyeing hair dyes.

Other and more detailed objects of this invention will be apparent from the following description and claims.

The class of nitrodiphenylamine dyes that are useful for the purpose of the present invention may be defined by the formula:

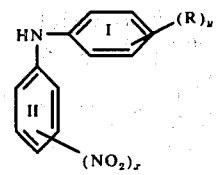

wherein:
R is an electron donor functional group;
$y$ is a whole number from 0 to 1 inclusive; and
$x$ is a whole number from 1 to 2 inclusive.

In a more particular aspect of this invention, the group $-(R)_y$ of Formula I may be more particularly defined as having the structure:

in which:
i. $r$ is a whole number from 0 to 1 inclusive;
ii. $x$ is an element having an atomic number from 7 to 8 inclusive which when present is bonded by one of its valences to a carbon of ring I;
iii. $R^1$ is lower aliphatic having a chain length of from 1 to 6 atoms and when present is bonded to X;
iv. $R^2$ is lower alkyl e.g. having 1 to 6 carbons which when present is bonded to a ring carbon of ring I;
v. H is hydrogen which when present is bonded to X;
vi. $a$ is a whole number from 0 to 1 inclusive;
vii. $b$ is a whole number from 0 to 2 inclusive;
viii. $c$ is a whole number from 0 to 2 inclusive;
ix. $d$ is a whole number from 0 to 1 inclusive; and
x. the sum of $a + b + c$ being no greater than 3 and $d$ being 0 when the sum of $a + b + c$ is greater than 0.

In still a more particular aspect of this invention, the group $-(R)_y$ in Formula I above may be described by the structure:

in which:
i. $r$, X, H, $R^2$, $a$, $b$ and $d$ have the same value ascribed to them in connection with Formula II;
ii. $R^3$ is lower alkyl having 1 to 6 carbons which when present is bonded to X;
iii. $R^4$ is lower hydroxyalkyl having 2 to 4 carbons and 1 to 3 hydroxy groups which when present is bonded to X;
iv. $e$ is a whole number from 0 to 2 inclusive;
v. $f$ is a whole number from 0 to 2 inclusive;
vi. the sum of $a + b + e + f$ being no greater than 3 and $d$ being 0 when the sum of $a + b + e + f$ is greater than 0.

As is apparent from the definitions given above, the nitrodiphenylamine dyes that are useful herein include both those dyes in which ring I carriers no substituents and those in which it carries one electron-donor (or electron-releasing) functional group. The presence of an electron-donor functional group has a virtue in that it appears to enhance the color of the dye. Although the presence of no more than one electron-donor functional group in ring I is preferred, the incorporation of more than one such functional in ring I may be made without departing from the spirit of this invention.

As is further noted from the formulas given above, benzene ring II may carry one or two nitro groups. However, in certain aspects of this invention the presence of one nitro group in ring II is preferred.

As will further be seen from the above formulas, when an electron-donor group is present it will be bonded either directly to a ring carbon of ring I as in the case when it is alkyl and through an atom X to a ring carbon of ring I when it is other than alkyl. X is defined as being an atom having an atomic number between 7 and 8 inclusive i.e. oxygen or nitrogen.

It will also be noted from the above formulas that the electron-donor functional group, when present on ring I, may occupy positions which are ortho, meta, or para to the amine nitrogen. Similarly when one nitro group is present on ring II, it may be present in the ortho, meta or para position. However, it has been found that best results are obtained with those dyes in which the electron-donor group on ring I is para to the amine nitrogen and the nitro group on ring II is ortho to the amine nitrogen.

As used herein the term electron-donor or electron-releasing substituent refers to a substituent which when bonded to a benzene nucleus tends to supply electrons to and to increase the electron density of the benzene nucleus. This is a term well known in the organic chemical art to define a fairly well circumscribed class of materials (See "Organic Chemistry" by Fieser & Feiser, third edition, 1956, Reinhold Publishing Corporation, New York pages 566 and 567). These substituents are, in general, alkyl, hydroxy, amino substituents or groups derived from these. By way of illustrating generally typical electron-donor substituents $(R)_y$ in Formula I above, mention may be made of the following: —$NH_2$; —N(lower alkyl)$_2$; —NH(lower alkyl); —N(lower hydroxyalkyl)$_2$; —NH(lower hydroxyalkyl); —N(lower alkyl) (lower hydroxyalkyl);

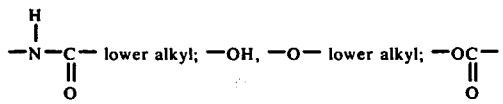

lower alkyl; -lower alkyl; etc. In these substituents lower alkyl is illustrated by alkyl having 1 to 6 carbons e.g. methyl, ethyl, n-propyl, i-propyl, n-butyl, tert-butyl, n-pentyl, n-hexyl. Lower hydroxyalkyl generally is illustrated by hydroxyalkyl having 2 to 4 carbon atoms and 1 to 3 hydroxy groups e.g. 2-hydroxyethyl, 3-hydroxypropyl, 2-hydroxypropyl, tris(hydroxymethyl)methyl; 1,3-dihydroxy-2-methyl-2-propyl; 2,3-dihydroxypropyl; 1,3-dihydroxy-2-propyl, etc.

Among the compounds that are used for the purposes of the present invention are classes of compounds which are novel. One such group of compounds may be defined by the formula:

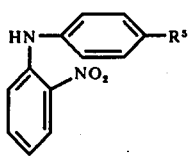

in which $R^5$ is OH, —NH(lower hydroxyalkyl), —N(-lower hydroxyalkyl)$_2$, —O lower alkyl. In this case lower hydroxyalkyl and lower alkyl have the same significance ascribed to them above. Of special interest and utility are the compounds of Formula IV wherein $R^5$ is —OH or —N(CH$_2$CH$_2$OH)$_2$.

Another class of novel compounds which are useful for the purposes of this invention may be described by the formula:

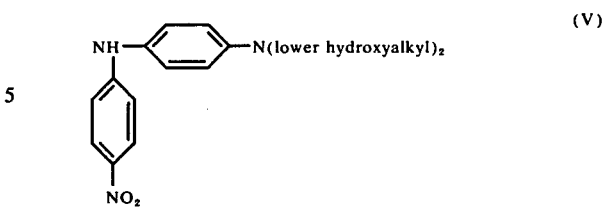

In this case too lower hydroxyalkyl has the same significance ascribed to it above e.g. having from 2 to 4 carbons and 1 to 3 hydroxy groups. Furthermore, the lower hydroxyalkyl substituents illustrated above may also serve as lower hydroxyalkyl substituents in Formula V. Of particular interest is the compound of Formula V in which the group —N(lower hydroxyalkyl)$_2$ is —N(CH$_2$CH$_2$OH)$_2$.

The advantage of the aforesaid dyes as employed in this invention lies in a combination of shade, affinity to hair, and wash fastness. They are, in general, in the range from yellow to orange and red. They can, therefore, for the most part be used to supply all or part of the red component in shades requiring it. Though they show only fair affinity for undamaged gray hair, they dye the damaged ends of hair sufficiently well. This is especially true of ends previously damaged by permanent waving, and to a lesser extent by bleaching. Moreover, they are, in general, faster to shampooing than existing reddish dyes. The net effect then is that when used with the blue dyes of the nitro-p-phenylenediamine class, they give on-tone (level, good union) dyeings of hair having permanent waved ends, and this shade stays on-tone during at least one subsequent shampooing.

In practice, the dyes employed in this invention would most often be used together with other red dyes which would supply most of the red component of the dye blend. However, in the yellower shades, they may replace the red component altogether.

In carrying out the present invention, any of the nitrodiphenylamine dyes described above or combinations thereof are incorporated in a fluid hair dye vehicle of the type suitable for applying direct-dyeing dyes. A large number of such vehicles are known to those in this art. These may vary from simple aqueous solutions and/or suspensions of the dye to very sophisticated aqueous compositions such as creams, lotions, pastes, gels, etc. containing blends of other dyes, non-ionic and anionic detergents, solvents, thickeners, perfumes, etc. In these aqueous compositions the carriers or vehicles may be water or a combination of water with other solvents, e.g. ethanol. It may also be employed in an aerosol system e.g. an aerosol emulsion system in which the dye is contained in an aqueous phase of the system.

The nitrodiphenylamine dyes employed in the present invention can be employed to prepare basic neutral or acidic dye compositions. Furthermore, they may likewise be included in hair dyeing compositions which contain other direct dyeing dyes. A variety of direct dyeing dyes is known in the prior art which are useful for this purpose. They include nitro dyes, azo dyes, anthraquinone dyes, etc. By way of illustration, any of the nitro dyes disclosed in the following U.S. Patents may be used in conjunction with the present dyes: U.S. Pat. Nos. 2,750,326; 2,750,327; 3,088,877; 3,088,878 and 3,088,978.

The pH of the present dye compositions can vary from about 4 to 12 and preferably from 7 to 11.5. Any selected water-dispersible, compatible, alkalizing agent (if it is desired to have the compositions in the alkaline range) can be used to give the desired pH. The quantity of the alkalizing agent employed can vary over a wide range depending on the dye and particular alkalizing agent employed and the desired pH. Illustratively, the alkalizing agent can vary from less than about .05% to about 10%, and preferably from about .10% to about 5% by weight of the composition.

Any of a wide variety of alkalizing agents can be used to adjust the pH of the present dyeing composition on the basic side. Ammonium hydroxide, because of its freedom from toxicity over a wide concentration range and its economy, is an acceptable alkalizing agent. However, there can be used in place of, or together with, ammonia any other compatible ammonia derivative as an alkalizing agent, such as an alkylamine, e.g. ethylamine, dipropylamine, or triethylamine; an alkanediamine, e.g. 1,3-diaminopropane; an alkanolamine, e.g. monoethanolamine or diethanolamine, triethanolamine; a polyalkylene polyamine, e.g. diethylenetriamine; or a heterocyclic amine, such as morpholine.

The pH of the composition may be adjusted on the acid side with any inorganic or organic acid or acid salt which is compatible with the composition and will not introduce toxicity under its conditions of use, especially when acid compositions are desired. Illustrative of acids or acid salts there can be mentioned: sulfuric, formic, acetic, lactic, citric or tartaric acid, or ammonium sulfate, sodium dihydrogen phosphate or potassium bisulfate.

Surface active agents can also be employed in the dyeing compositions of this invention. These can be anionic, non-ionic or cationic. By way of examples of the various types of surface active agents, there can be mentioned: higher alkylbenzene sulfonates; alkyl-naphthalenesulfonates; sulfonated esters of alcohols and polybasic acids; taurates; fatty alcohol sulfates; sulfates of branched chain or secondary alcohols; alkyl dimethylbenzyl ammonium chlorides; salts of fatty acids or fatty acid mixtures; N-oxyalkylated fatty acid alkanolamides; and the like. Illustrative of specific surfactants there can be mentioned: sodium lauryl sulfate; polyoxyethylene lauryl ester; myristyl sulfate; glyceryl monostearate; triethanolamine oleate; sodium salt of palmitic methyl taurine; cetyl pyridinium chloride; lauryl sulfonate; myristyl sulfonate; lauric diethanolamide; polyoxyethylene stearate; ethoxylated oleyl diethanolamide; stearyl dimethyl benzyl ammonium chloride; dodecyl benzene sodium sulfonate; triethanolamine salt of p-dodecylbenzene sulfonate; triethanolamine salt of p-dodecylbenzene sulfonate; nonyl naphthalene sodium sulfonate; dioctyl sodium sulfosuccinate; sodium N-methyl-N-oleoyl taurate; oleic acid ester of sodium isothionate; sodium dodecyl sulfate; the sodium salt of 3,0-diethyl tridecanol-6-sulfate and the like. The quantity of surface active agent can vary over a wide range, such as that of from about 0.05% to 15% and preferably from about 0.10% to 5% by weight of the composition.

A thickening agent may also be incorporated in the dyeing composition of this invention which may be one or several of those commonly used in hair dyeing. These are exemplified by such thing as sodium alginate or gum arabic, or cellulose derivatives, such as methylcellulose e.g. Methocel 60HG, or the sodium salt of carboxymethylcellulose, or hydroxyethylcellulose e.g. CELLOSIZE QP-40 or acrylic polymers, such as polyacrylic acid sodium salt, or inorganic thickeners, such as bentonite. The quantity of this thickening agent can also vary over a wide range, such as that of from about 0.1% to 20%, ordinarily it will range from about 0.5% to 5% by weight of the composition.

It is also useful to incorporate an antioxidant in the present dye compositions. A variety of antioxidants are known in the prior art which would be useful for this purpose. Among these mention may be made of the inorganic sulfites, e.g. sodium sulfite, thioglycollic acid and other mercaptans, butylated hydroxy toluene, sodium dithionite, various forms of ascorbic acid and its derivatives e.g. sodium ascorbate, erythrobic acid, ascorbyl palmitate, ascorbyl laurate, etc. The quantity of antioxidant when in use can vary quite a bit. However, this will, in general, be of the order of about .025% to 1% by weight.

The nitrodiphenylamine dyes are incorporated in compositions of this invention in tinctorially effective quantities i.e. in concentrations which are adequate to color the hair. These quantities can vary over a wide range, but ordinarily they will constitute from about 0.001% to greater than about 5% e.g. 10% by weight of the composition. However, preferably, it will comprise from about 0.001% to about 2% by weight of the composition. The major constituent of the composition employed is usually water, and this can vary in amount over a wide range dependent in large measure on the quantity of other additives. Thus, the water content can be as little as 10%, but preferably will amount to from about 70% to 99% by weight of the composition.

The dyeing compositions of this invention are preferably aqueous compositions. The term aqueous composition is used herein in its usual generic sense as embracing any water-containing composition useful for the present purposes. This includes true solutions of the dye in an aqueous medium, either alone or in conjunction with other materials, which are also dissolved or dispersed in the aqueous medium. The term aqueous composition also encompasses any mixture of dye with the aqueous medium either alone or together with other ingredients. The dye may be colloidally dispersed in the medium or may merely be intimately mixed therein. Moreover, the aqueous medium may comprise water or water and an additional or auxilliary solvent. The latter may be employed as a common solvent to enhance the solubility of the dye or some other organic material. Other auxilliary solvents which may be used for this purpose include ethanol, carbitol, isopropanol, propylene glycol, ethylene glycol, glycerine, etc.

Typical dyeing compositions of the simple aqueous alkaline variety described above are set forth below:

| AQUEOUS ALKALINE COMPOSITIONS | | |
|---|---|---|
| | General Range | Preferred Range |
| Nitrodiphenylamine dye | .001 – 5 % | .001 – 2% |
| Surface active agents | 0.05 – 15% | 0.10 – 5% |
| Alkali | 0.05 – 10% | 0.10 – 5% |
| Thickening Agent | 0.1 – 20% | 0.5 – 5% |
| Water | QS to 100% | QS to 100% |
| pH (acid added if necessary) | 7.0 – 11.5 | 7.5 – 10.5 |

The nitrodiphenylamine dye and any of the surface active agents, thickening agents, and combinations thereof set forth above may be used in the proportions specified in the table immediately above. The alkali in these compositions will be any one or more of the alkalizing agents described above.

The simple aqueous alkaline dyeing compositions of this invention can be prepared by the conventional methods used in the hair dyeing art. Thus, they can be prepared by dissolving or suspending the dye in water in the desired concentrations. Water miscible organic solvents e.g. ethanol can be employed to facilitate solution of the dye. In this event, the dye can be dissolved first in the solvent and this solution is then diluted with water. The dispersion of the various ingredients can also be facilitated by heating the composition at temperatures varying from 40° to 110° C, either before dilution with water or afterwards.

These compositions can be applied to hair by the conventional techniques used in this art. Illustratively, when applied to living hair on the human head, the compositions can be applied to the hair with a brush, sponge, or other means of contact, such as pouring the composition directly onto the hair until saturated. The reaction time or time of contact of the dyeing composition with the hair is not critical and can vary over a wide range used in the hair dyeing art, such as periods of about 5 minutes to about 2 hours. Preferably, a period of from about 5 minutes to about 60 minutes is utilized and most often a period of 10 to 30 minutes. The dyeing temperature can vary over wide limits as is conventional in the art. Thus, the dyeing temperature can vary from about room temperature, e.g. about 20° to about 60° C, and preferably from about 20° to about 45° C.

As previously mentioned, the present invention is also applicable to aerosol systems containing an aqueous phase which has incorporated therein said nitrodiphenylamine dyes. In this aspect of the invention an aqueous alkaline composition, as described above, is prepared and serves as the aqueous concentrate which is incorporated in the aerosol system. In preparing the aerosol direct dyeing dye composition of this invention, the alkaline concentrate described above (97% to 90% by weight) is mixed with a propellant (3% to 10% by weight). In a preferred form of this aspect of the invention, the propellant comprises about 5% by weight of the total aerosol composition, the balance being made up of concentrate.

Any of a variety of propellants well known to those skilled in the art may be used in this aspect of the invention. As used herein, the term propellant means propellant system which may comprise a single propellant component or a combination of propellant components. It is well known in the aerosol art that it is often advantageous to use a mixture of fluorocarbon propellants or the combination of a hydrocarbon propellant and a fluorocarbon propellant to obtain the special benefits which the single component propellants do not exhibit.

In preparing aerosol composition encompassed in the present invention any of a variety of propellants may be used e.g. gases or low boiling liquids. It may be a fluorinated or a fluorochlorinated lower saturated aliphatic hydrocarbon, and preferably a halogenated alkane containing not more than 2 carbon atoms and at least 1 fluorine atom, or mixtures thereof. The preferred halogenated lower alkane compounds may be represented, generally, by the formula $C_mH_nCL_yF_z$, wherein $m$ is an integer less than 3, $n$ is an integer or zero, $y$ is an integer or zero, and $z$ is an integer, such that $n + y + z = 2_m + 2$. It may also be a liquefied hydrocarbon gas, e.g. butane, isobutane, propane, etc. These may be used along or admixed with each other. In addition, they may also be employed in admixture with the halogenated propellants mentioned above.

The propellants should preferably possess a boiling point of less than 75° F at 760 mm. pressure. Typical examples of useful propellants are dichlorodifluoromethane ("Freon 12"), dichlorotetrafluoroethane ("Freon 114"), $CClF_2$—$CClF_2$, trichloromonofluoromethane ("Freon 11"), dichloromonofluoromethane ("Freon 21"), monochlorotrifluoromethane ("Freon 13"), $CCl_2$–$CClF_2$ ("Freon 113"), or 1,1-difluoroethane ("Freon 152A").

In preparing the aerosol composition of this invention, the direct dye alkaline concentrate containing said nitrodiphenylamine is formulated in the usual manner well known to those skilled in the art and then the desired propellant is added to it. This may be accomplished by either of two methods. One such method involves the so-called "cold filling" wherein the concentrate and propellant are mixed in the cold and then added to the aerosol can which is then capped with an aerosol valve. In another procedure, the direct dye concentrate is charged into a can which is capped with an aerosol valve. The instant propellant blend is then pressure filled through the aerosol valve.

In employing the aerosol compositions of the present invention, in dyeing hair the procedure for use is as follows: shake can well to obtain maximum emulsification or solution of propellant. Hold can so that applicator nozzle is close to the hair. Apply foam and work thoroughly through hair. Allow color to develop on the hair (e.g. 10 to 30 minutes) and then wash excess color solution off the hair.

The following Examples are further illustrative of the present invention. It is to be understood, however, that the invention is not limited thereto.

EXAMPLE 1

Preparation of 4'-hydroxy-2-nitro-diphenylamine

Reaction:

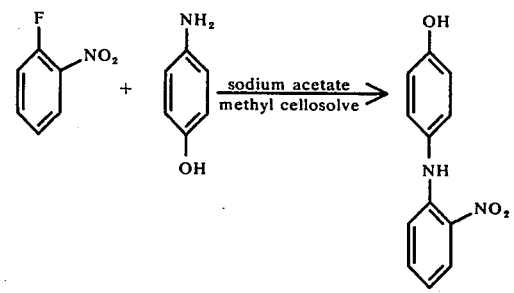

Starting Material:
A. 141 g. (1M) ortho-fluoronitrobenzene
B. 109 g. (1M) para-aminophenol
C. 136 g. (1M) sodium acetate 0.3H$_2$O
D. 350 ml. methyl cellosolve (2-methoxyethanol)

Procedure:
A, B, C and D placed in a 2 liter 3 neck flask equipped with a stirrer and a reflux condenser. The reaction is heated by means of a heating mantle, with stirring, to reflux (about 115° C) for 23 hours. The reaction is allowed to cool to room temperature and the resulting mixture is filtered. Solid that is obtained is a salt residue and is discarded. The filtrate is evaporated of solvent on a rotary evaporator. The resulting solid is recrystallized from aqueous ethanol (50/50). Weight of pure product obtained = 189 g. m.p. = 144°–145.5° C., % yield = 82.2%.

EXAMPLE 1A

Preparation of 4′-hydroxy-2-nitro-diphenylamine

Reaction:

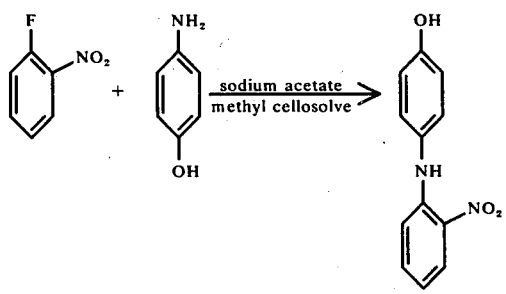

Starting Material:
A. 28.2 g. (0.2M) ortho-fluoronitrobenzene
B. 21.8 g. (0.2M) p-aminophenol
C. 27.2 g. (0.2M) sodium acetate 0.3H$_2$O
D. 70 ml. methyl cellosolve
Procedure.

A, B, C and D are mixed in a small autoclave and heated to 170°–180° C for 28 hours. The reaction mixture was then cooled and filtered. The filtrate was evaporated of solvent on a rotovac and the resulting solid was recrystallized from a mixture of ethanol and water (50/50). 33.3 grams (75% yield) of a red brown crystalline material was obtained having a melting point in a range of 140°–141° C.

EXAMPLE 2

Preparation of 3′-hydroxy-2-nitro-diphenylamine

Reaction:

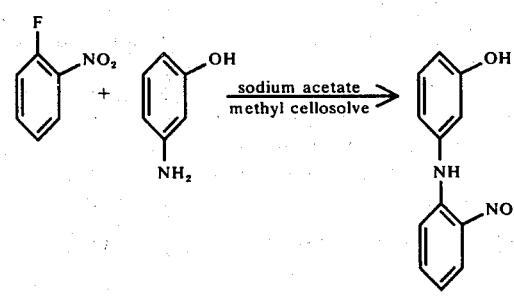

Starting Material:
A. 28.2 g. (0.2M) o-fluoronitrobenzene
B. 21.8 g. (0.2M) m-aminophenol
C. 27.2 g. (0.2M) sodium acetate 0.3H$_2$O
D. 70 ml. methyl cellosolve (2-methoxyethanol)
Procedure:

A, B, C and D mixed in a 500 ml. 3 neck flask equipped with a stirrer and reflux condenser. The reaction mixture is heated by means of a heating mantle, with stirring, to reflux (about 115° C) for 23 hours. The reaction is cooled to room temperature and filtered. The solid salt residue is discarded. The filtrate is evaporated of solvent on a rotary evaporator. The resultant pasty mass is recrystallized from aqueous ethanol (50/50). Wt. of pure product obtained = 33.36 g. m.p. = 131°–133° C. Dyes hair yellow.

EXAMPLE 3

Preparation of 2′-hydroxy-2-nitro-diphenylamine

Reaction:

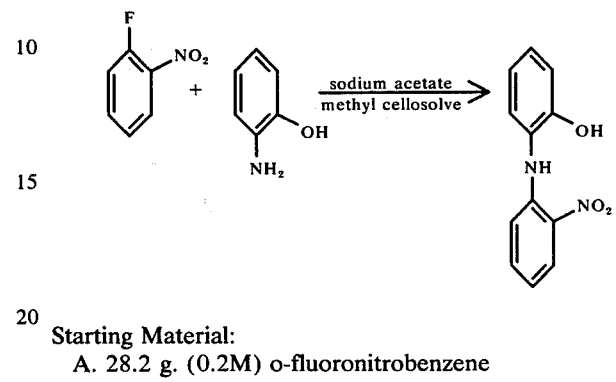

Starting Material:
A. 28.2 g. (0.2M) o-fluoronitrobenzene
B. 21.8 g. (0.2M) o-aminophenol
C. 27.2 g. (0.2M) sodium acetate 0.3H$_2$O
D. 70 ml. methyl cellosolve (2-methoxyethanol)
Procedure:

Same exact method as used in Example 2.
Weight of product obtained = 26.35 g. m.p. = 116–120° C. Dyes hair yellow-orange.

EXAMPLE 4

Preparation of 4′-hydroxy-4-nitro-diphenylamine

Reaction:

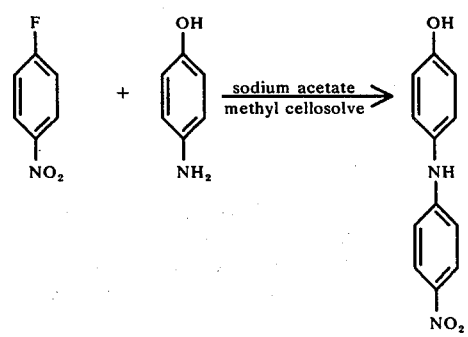

Starting Material:
A. 28.2 g. (0.2M) p-fluoronitrobenzene
B. 21.8 g. (0.2M) p-aminophenol
C. 27.2 g. (0.2M) sodium acetate .3H$_2$O
D. 75 ml. methyl cellosolve (2-methoxyethanol)
Procedure:

A, B, C and D mixed in a 500 ml. 3 neck flask equipped with a stirrer and reflux condenser. The reaction mixture is heated by means of a heating mantle, with stirring, to reflux (approximately 115° C) for 7 hours. The reaction is cooled to room temperature and filtered. The solid salt residue is discarded. The filtrate is evaporated of solvent on a rotary evaporator. The resultant product is recrystallized from aqueous ethanol (50/50). Thin layer chromatogram indicates impurities still present. Solid treated with 25% aqueous sodium hydroxide and extracted with benzene. The water layer is neutralized with concentrated hydrochloric acid and concentrated ammonium hydroxide. Resulting red solid filtered and dried. Weight of product obtained = 21.0 g. m.p. = 178°–180° C. Dyes hair yellow.

EXAMPLE 5

Preparation of 4'-hydroxy-2,6-dinitro-diphenylamine
Reaction:

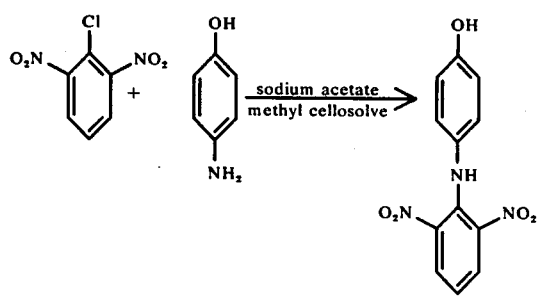

Starting Material:
A. 40.4 g. (0.2M) 1-chloro-2,6-dinitrobenzene
B. 21.8 g. (0.2M) p-aminophenol
C. 27.2 g. (0.2M) sodium acetate 0.3H$_2$O
D. 75 ml. methyl cellosolve (2-methoxyethanol)
Procedure:
Same exact method as used in Example 4. Product is pure after recrystallization from aqueous ethanol. Alkali treatment is unnecessary. Weight of product = 13.5 g. m.p. = 204.5°–205.5° C. Dyes bleached hair orange.

EXAMPLE 6

Preparation of 4'-methoxy-2-nitro-diphenylamine
Reaction:

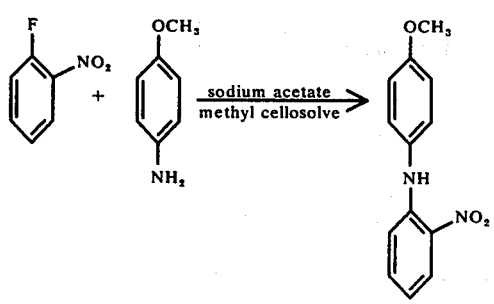

Starting Material:
A. 28.2 g. (0.2M) o-fluoronitrobenzene
B. 24.6 g. (0.2M) p-anisidine
C. 27.2 g. (0.2M) sodium acetate 0.3H$_2$O
D. 70 ml. methyl cellosolve (2-methoxyethanol)
Procedure:
Same method as described in Example 2, except for reducing the reflux time to 18 hours instead of 23.
Weight of product = 28.5 g. m.p.= 88°–90° C. Dyes hair yellow.

EXAMPLE 7

Preparation of 4'(N,N-bis-β-hydroxyethylamino)-2-nitro-diphenylamine
Reaction:

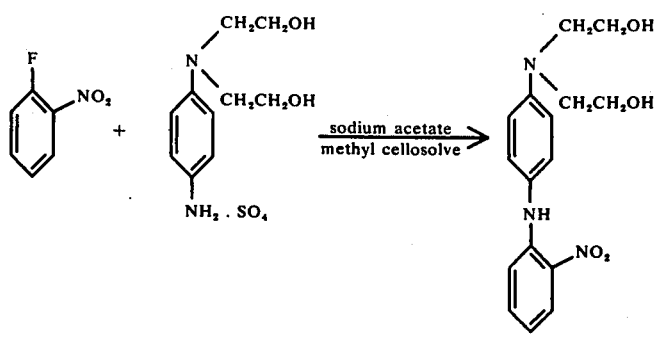

Starting Material:
A. 14.1 g. (0.1M) o-fluoronitrobenzene
B. 28.8 g. (0.1M) N,N(bishydroxyethyl)-p-phenylene diamine sulfate
C. 40.8 g. (0.3M) sodium acetate 0.3H$_2$O
D. 70 ml. methyl cellosolve (2-methoxyethanol
Procedure:
A, B, C and D mixed in a 500 ml 3 neck flask equipped with a stirrer and reflux condenser. Reaction mixture is heated by means of a heating mantle, with stirring, to reflux (approximately 108° C) for 22 hours. The reaction is cooled to room temperature and filtered. The solid salt residue is discarded. The filtrate is evaporated of solvent on a rotary evaporator. This tacky mass recrystallized from aqueous ethanol (50/50). A tacky solid forms which solidifies on ice-bath cooling and scratching. Thin layer chromatogram indicates a violet impurity, which is B. The solid is dissolved in ethyl acetate and extracted with water. B impurity soluble in water layer. Ethyl acetate layer treated with charcoal, filtered and filtrate evaporated. Resulting sticky product is dried on a porous plate, followed by drying in a dessicator. Weight of product = 21.4 g. m.p.(fast) = 100°–105° C. Dyes hair an orange brown.

EXAMPLE 8

Preparation of 4'-bishydroxyethylamino-2-nitro-diphenylamine
Reaction:

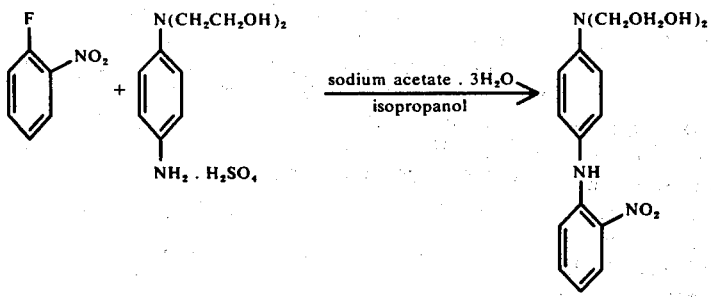 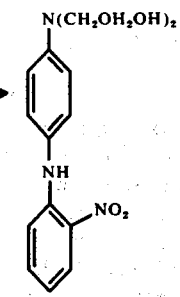

Starting Material:
A. 70.5 g. (0.5M) o-fluoronitrobenzene
B. 144.0 g. (0.5M) N,N-(bishydroxyethyl)-p-phenylenediamine sulfate
C. 204.0 g. (1.5M) sodium acetate 0.3H$_2$O
D. 375 ml. isopropanol Procedure:

A, B, C and D placed in a 1 liter 2 neck flask and heated to reflux with stirring for 4 hours. Reaction mixture was then cooled and filtered to eliminate salt. Resulting filtrate was steam distilled to eliminate all traces of o-fluoronitrobenzene. The hot contents of the flask were then transferred to a beaker and cooled with stirring. The solid that forms is filtered and subsequently this solid is treated with distilled water, stirred, filtered and washed. This purified procedure of washing with water is repeated twice. Product dried in 50° C oven overnight. Weight of product = 88.1 g. m.p. = 102°–105° C. Yield = 55.6%

EXAMPLE 9

Preparation of 2-nitro-4'-aminodiphenylamine

Reaction:

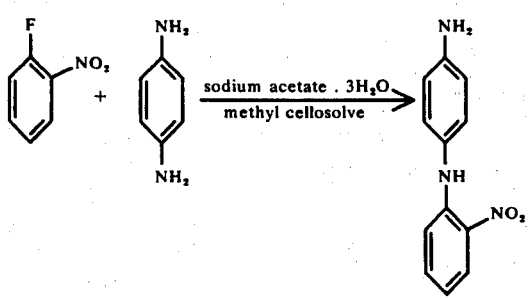

Starting Material:
A. 141 g. (1M) o-fluoronitrobenzene
B. 118 g. (1.10M) p-phenylenediamine
C. 136.0 g. (1M) Na acetate 0.3H$_2$O
D. 350 ml. methyl cellosolve Procedure:

A, B, C and D were mixed in a flask and heated at reflux (115° C) with stirring for 6½ hours. The reaction mixture was cooled during the night and filtered giving solid crystals of dye mixed with NaF. The crystals were washed with water to eliminate the salt. The crystalline product weighed after drying 137.6 g. m.p. 110°–111° C. The product was pure as the thin layer chromatogram indicated. (From the filtrate after steam distillation 83.3 g. of a less pure material recovered). 4-amino-2'-nitro-diphenylamine dyes gray hair orange. The literature: Bandrowsky C. 1900, II 852, Beilstein 13 p. 78 gives a m.p. of 105°–106° C for this compound. The experiment of this reference was repeated in which p-phenylenediamine = 2-bromonitrobenzene is autoclaved. This procedure gives an impure product.

EXAMPLE 10

Preparation of 4'-methylamino-2-nitrodiphenylamine

Reaction:

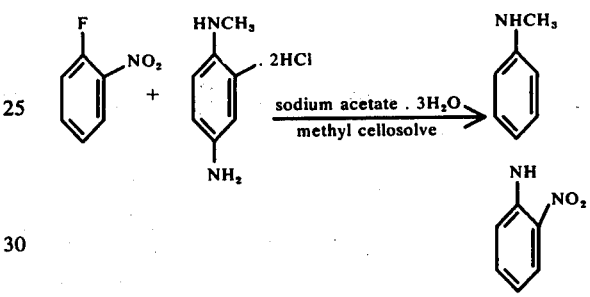

Starting Material:
A. 14.1 g. (0.1M) o-fluoronitrobenzene
B. 19.5 g. (0.1M) N-methyl-p-phenylenediamine
C. 40.8 g. (0.3M) sodium acetate 0.3H$_2$O
D. 100 ml. methyl cellosolve Procedure:

A, B, C and D are mixed in 500 ml. flask and heated to reflux (112° C) for 6 hours, cooled and filtered. Some solid separates which was treated with water and filtered to eliminate the salt. Red black crystals that was formed were dried. (M.P. of product = 89°–90° C. wt. = 4.4 g.) The above methyl cellosolve filtrate was steam distilled to eliminate o-fluoronitrobenzene. The solid remaining after steam distillation was filtered and washed with water to give an additional 16.1 g. of product. This is an orange dye.

EXAMPLE 11

Preparation of 4'-methyl-2-nitrodiphenylamine

Reaction:

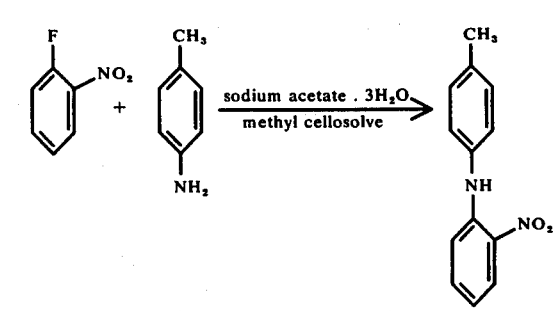

Starting Material:

A. 28.2 g. (0.2M) o-fluoronitrobenzene
B. 21.4 g. (0.2M) p-toluidine
C. 27.2 g. (0.2M) sodium acetate 0.3H$_2$O
D. 100 ml. methyl cellosolve Procedure:

A, B, C and D were mixed in 500 ml. flask, heated to reflux for 4 ½ hours, cooled and filtered. A small amount of salt separates. The filtrate was steam distilled. The residual material was transferred to a beaker and allowed to cool. An orange solid forms on cooling which was filtered and dried in air. M.P. of product = 69°–70° C. Thin layer chromatogram indicates pure product. Wt. of product = 27.3 g. This was used to dye hair samples and gives a yellow color.

EXAMPLE 12

Preparation of 3'-amino-2-nitrodiphenylamine

Reaction:

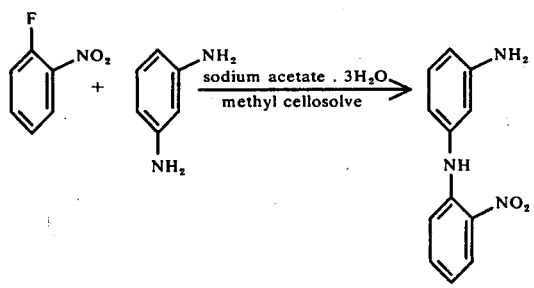

Starting Material:
A. 28.2 g. (0.2M) o-fluoronitrobenzene
B. 21.6 g. (0.2M) m-phenylenediamine
C. 27.2 g. (0.2M) sodium acetate 0.3H$_2$O
D. 100 ml. methyl cellosolve Procedure:

A, B, C and D were mixed in 500 ml. flask, heated to reflux (120° C) for 6 hours, cooled overnight and filtered. Solid material that separated was treated with water to eliminate salt leaving 3.5 g. of orange-red crystals (m.p. 160–162). This product is an orange-yellow hair dye.

EXAMPLE 13

Preparation of 2'-amino-2-nitrodiphenylamine

Reaction:

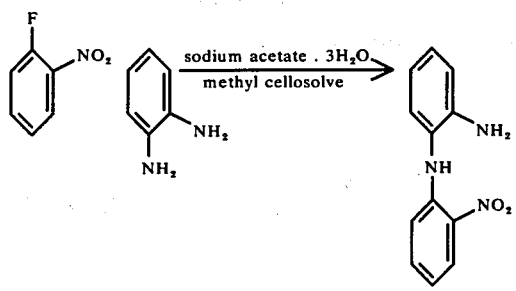

Starting Material:
A. 28.2 g. (0.2M) o-fluoronitrobenzene
B. 21.6 g. (0.2M) o-phenylenediamine
C. 27.2 g. (0.2M) sodium acetate 0.3H$_2$O
D. 100 ml. methyl cellosolve Procedure:

A, B, C and D were mixed in 500 ml. flask, heated to reflux for 6 hours, cooled overnight and filtered. Large amounts of solid separates. This solid is treated with water to eliminate salt. The resulting yellow crystals were dried, giving 11.8 g. of orange yellow crystals (m.p. 107–108). This is an orange-yellow dye which can be used to dye hair.

EXAMPLE 14

Preparation of 2-nitrodiphenylamine

Reaction:

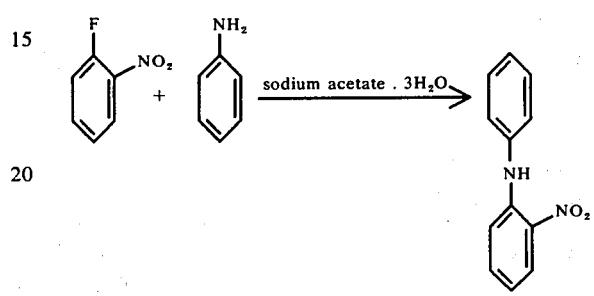

Starting Material:
A. 28.2 g. (0.2M) 1-fluoro-2-nitrobenzene
B. 46.5 g. (0.5M) aniline
C. 27.2 g. (0.2M) sodium acetate 0.3H$_2$O Procedure:

A, B and C were treated in a small autoclave at 170°–180° C for 28 hours, cooled and filtered. Recrystallized from ethyl alcohol and water (50/50). M.P. = 72.5°–73.5° C. Wt. of product = 35.7 g.

DYEING EXAMPLES

TABLE I

| Ingredients | Ex.A % by wt. | Ex.B % by wt. | Ex.C % by wt. |
|---|---|---|---|
| 4'-hydroxy-1-nitro-diphenylamine | .25 | — | — |
| 4'(N,N-bis-β-hydroxyethyl-amino)-2-nitro-diphenylamine | — | .25 | — |
| 4'-hydroxy-4-nitro-diphenylamine | — | — | .25 |
| Diethanolamine | 2.000 | 2.000 | 2.000 |
| Carbitol | 4.000 | 4.000 | 4.000 |
| Lauric Diethanolamide | 3.000 | 3.000 | 3.000 |
| Triethanolamine Linear Alkylate Sulfonate | 0.500 | 0.500 | 0.500 |
| Polyoxyethylene Hydrogenated Fatty Amide | 1.900 | 1.900 | 1.900 |
| Sodium Carboxymethyl Cellulose | 2.400 | 2.400 | 2.400 |
| Oleic Acid | 1.000 | 1.000 | 1.000 |
| Perfume | 0.125 | 0.125 | 0.125 |
| Water q.s. | 100.000 | 100.000 | 100.000 |
| pH | 9.5 | 9.5 | 9.5 |

The compositions of Examples A, B and C are applied to swatches of undamaged gray hair and permanent-waved hair at 38° C., allowed to remain for 20 minutes, then rinsed off with lukewarm water.

TABLE II

| Composition | Shade on Hair | Affinity Gray Hair | Affinity Permanent Waved |
|---|---|---|---|
| Example A | Orange | Fair | Good |
| Example B | Dull Orange | Poor | Fair |
| Example C | Yellow | Good | Good |

The dyeings were moderately fast to shampooing.

TABLE III

| Ingredients | Ex.D | Ex.E | Ex.F | Ex.G | Ex.H | Ex.I |
|---|---|---|---|---|---|---|
| 4'-hydroxy-1-nitrodiphenylamine | — | .1 | .05 | — | — | — |
| 4'(N,N-bis-β-hydroxyethylamino)-2-nitro-diphenylamine | .05 | — | — | .16 | — | .25 |
| 4'-hydroxy-4-nitro-diphenylamine | — | — | — | — | .21 | — |
| Diethanolamine | 2.00 | 2.00 | 2.00 | 2.00 | 2.00 | 2.00 |
| Carbitol | 4.00 | 4.00 | 4.00 | 4.00 | 4.00 | 4.00 |
| Lauric Diethanolamide | 1.50 | 1.50 | 1.50 | 1.50 | 1.50 | 1.50 |
| Triethanolamine salt of p-docecylbenzene-sulfonate | 0.50 | 0.50 | 0.50 | 0.50 | 0.50 | 0.50 |
| $CH_3(CH_2)_7CH=CH(CH_2)_7CON[(CH_2CH_2O)_{25}H]_2$ | 1.90 | 1.90 | 1.90 | 1.90 | 1.90 | 1.90 |
| Methylcellulose* | 2.40 | 2.40 | 2.40 | 2.40 | 2.40 | 2.40 |
| Oleic Acid | 1.00 | 1.00 | 1.00 | 1.00 | 1.00 | 1.00 |
| Perfume | 0.125 | 0.125 | 0.125 | 0.125 | 0.125 | 0.125 |
| Water q.s. | 100.00 | 100.00 | 100.00 | 100.00 | 100.00 | 100.00 |
| pH adjusted to | 9.6 | 9.6 | 9.6 | 9.6 | 9.6 | 9.6 |

*Methylcellulose referred to herein and elsewhere is characterized as follows: methoxyl content 27.5 to 31.5%; viscosity of 2% aqueous solution at 20° C in Centipoise 1500; average M.W. 63,000.

If desired, the perfume may be omitted from any of the compositions of Examples D through I.

The following Examples further illustrate the use of a gel base and a cream base which serve as the vehicle for the nitrodiphenylamine dye. The dyes employed in these Examples are each of the dyes which are prepared in accordance with Examples 1 through 14 above.

TABLE IV

| Ingredients | Ex. J | Ex. K |
|---|---|---|
| Dye | .030 | 0.060 |
| Diethanolamine | — | 0.800 |
| Triethanolamine | 2.750 | — |
| Carbitol | 5.000 | 3.500 |
| Lauric Diethanolamide | 3.000 | 1.800 |
| Polyoxyethylene Hydrogenated Fatty Amide | 1.800 | 1.500 |
| Na-Carboxymethyl Cellulose | 4.200 | 2.800 |
| Oleic Acid | 1.500 | 2.000 |
| Perfume | 0.100 | 0.125 |
| Water q.s. | 100.000 | 100.000 |
| pH adjusted to | 9.0 | 8.0 |

TABLE V

| Ingredients | Ex.L | Ex.M | Ex.N | Ex.O | Ex.P | Ex.Q | Ex.R | Ex.S |
|---|---|---|---|---|---|---|---|---|
| 4'-hydroxy-2-nitrodiphenylamine | 0.1 | — | 0.1 | 0.1 | — | 0.1 | — | 0.1 |
| 4'-bis(3-hydroxyethylamino)-2-nitrodiphenylamine | — | 0.2 | — | — | 0.2 | — | 0.2 | — |
| Ethyl alcohol | 5.0 | 5.0 | 5.0 | — | — | — | — | — |
| Diethylene glycol monoethyl ether | — | — | — | 5.0 | 5.0 | 5.0 | 5.0 | 5.0 |
| Hexadecyltrimethyl ammonium chloride | 2.0 | — | 1.0 | 2.0 | — | 1.0 | — | — |
| Octadecenyltrimethyl ammonium chloride | — | 1.8 | 0.9 | — | 1.4 | 0.9 | 1.5 | 1.5 |
| Octadecadienyltrimethyl ammonium chloride | — | — | — | — | — | — | 1.5 | 1.5 |
| Ethoxylated (50 moles E.O.) oleyl diethanolamide | 2.0 | 2.0 | — | — | 1.5 | 1.0 | 2.5 | 2.5 |
| Ethoxylated (50 moles E.O.) palmityl diethanolamide | — | — | 2.0 | 2.0 | 0.5 | 1.0 | — | — |
| Monoethanolamine | 0.4 | 0.4 | 0.4 | — | — | — | — | — |
| Diethanolamine | — | — | — | 0.71 | 0.71 | 0.71 | 0.71 | 0.71 |
| Citric acid | 0.5 | 0.5 | 0.5 | 0.5 | 0.5 | 0.5 | 0.5 | 0.5 |
| Methylcellulose | 2.0 | 2.0 | 2.0 | 2.0 | 2.0 | 2.0 | 2.0 | 2.0 |
| Perfume | 0.1 | 0.1 | 0.1 | 0.1 | 0.1 | 0.1 | 0.1 | 0.1 |
| pH | 5.7 | 5.7 | 5.7 | 5.7 | 5.7 | 5.7 | 5.7 | 5.7 |
| Water | q.s. to 100% ⟶ | | | | | | | |

The dye compositions of Table V are applied to human hair (the hair may be dry or slightly wet) and are spread uniformly throughout, insuring that no areas are omitted. The compositions are allowed to remain on the hair for ten to thirty minutes then thoroughly rinsed out of the hair with water. The hair is then allowed to dry.

Although the invention has been described with reference to specific forms thereof, it will be understood that many changes and modifications may be made without departing from the spirit of this invention.

What is claimed is:

1. A compound useful for a hair dye of the formula:

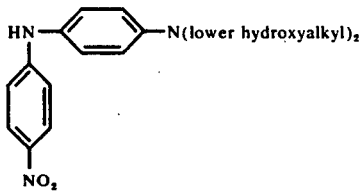

wherein said hydroxyalkyl groups have 2 to 4 carbon atoms and 1 to 3 hydroxy groups.

2. The compound of claim 1 in which —N(lower hydroxyalkyl)$_2$ is —N(CH$_2$CH$_2$OH)$_2$.

3. A compound useful for a hair dye of the formula:

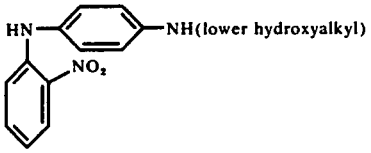

wherein said hydroxyalkyl group has from 2 to 4 carbon atoms and 1 to 3 hydroxy groups.

4. A compound useful for a hair dye of the formula:

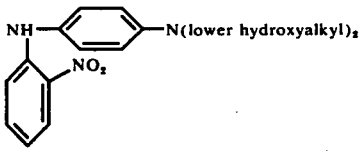

wherein said hydroxyalkyl groups have 2 to 4 carbon atoms and 1 to 3 hydroxy groups.

5. The compound according to claim 4 in which —N(lower hydroxyalkyl)$_2$ is —N(CH$_2$CH$_2$OH)$_2$.

UNITED STATES PATENT OFFICE
CERTIFICATE OF CORRECTION

Patent No. 4,021,486  Dated May 3, 1977

Inventor(s) Alexander Halasz et al.

It is certified that error appears in the above-identified patent and that said Letters Patent are hereby corrected as shown below:

Column 14, line 14, "=" should read -- + --.

Signed and Sealed this nineteenth Day of July 1977

[SEAL]

Attest:

RUTH C. MASON
*Attesting Officer*

C. MARSHALL DANN
*Commissioner of Patents and Trademarks*